United States Patent [19]
Dunn et al.

[11] 4,172,949
[45] Oct. 30, 1979

[54] 2,4-DISUBSTITUTED-5-OXO-5H-DIBENZO[a,d]CYCLOHEPTENES

[75] Inventors: James P. Dunn, Palo Alto; Peter H. Nelson; Karl G. Untch, both of Los Altos, all of Calif.

[73] Assignee: Syntex (U.S.A.) Inc., Palo Alto, Calif.

[21] Appl. No.: 920,047

[22] Filed: Jun. 28, 1978

[51] Int. Cl.$^2$ ............... C07C 65/14; C07C 69/76
[52] U.S. Cl. ............... 560/53; 560/17; 560/126; 562/461; 562/463; 546/203; 424/267; 424/308; 424/317
[58] Field of Search ............... 560/9, 53; 562/461, 562/462, 463

[56] References Cited
U.S. PATENT DOCUMENTS

| 3,933,905 | 1/1976 | Brunet et al. | 562/461 |
| 4,020,094 | 4/1977 | Nelson et al. | 562/405 |

Primary Examiner—James O. Thomas, Jr.
Assistant Examiner—L. Hendriksen
Attorney, Agent, or Firm—Alan M. Krubiner

[57] ABSTRACT

Compounds of the formula

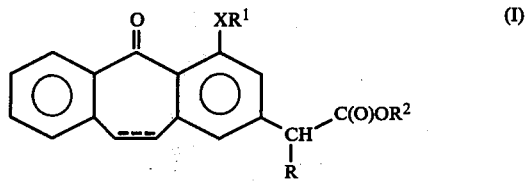

wherein R is hydrogen or methyl; $R^1$ is hydrogen, $C_1$ to $C_8$ linear or branched alkyl or $C_1$ to $C_8$ linear or branched alkanoyl; X is oxygen or sulfur; $R^2$ is selected from the group hydrogen, $C_1$ to $C_{18}$ linear or branched alkyl and the radicals —$(CH_2)_n$—$NR^3R^4$, —$CH_2$—$CH(OH)$—$CH_2$—$OH$ or a ketal thereof formed from the aldehyde or ketone $R^5R^6CO$, wherein $R^3$ and $R^4$ are each independently $C_1$ to $C_6$ linear or branched alkyl or $R^3$ and $R^4$ taken together with the nitrogen atom of the first radical are attached to form a 5- or 6-membered heterocyclic ring, $R^5$ and $R^6$ are each independently hydrogen, $C_1$ to $C_6$ linear or branched alkyl, phenyl or benzyl or $R^5$ and $R^6$ taken together represent an alkylene bridge of from 4 to 6 carbon atoms; n is an integer of from 2 to 4; and the dotted line represents an optional double bond; and the pharmaceutically acceptable salts thereof. The compounds have anti-inflammatory, analgesic and anti-pyretic activities and, accordingly, are useful in the treatment of inflammation, pain and/or pyrexia.

12 Claims, 2 Drawing Figures

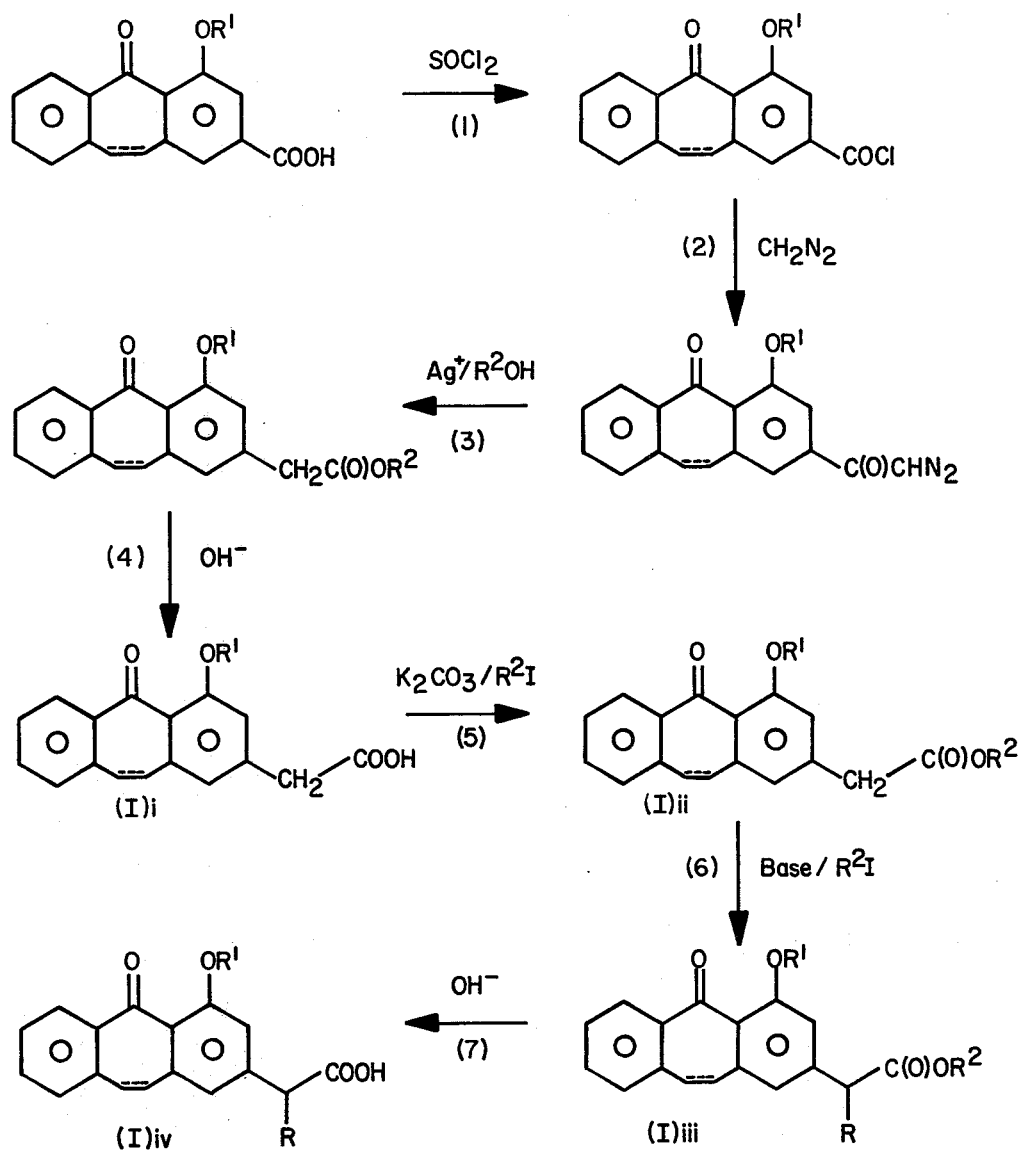
FIG_1
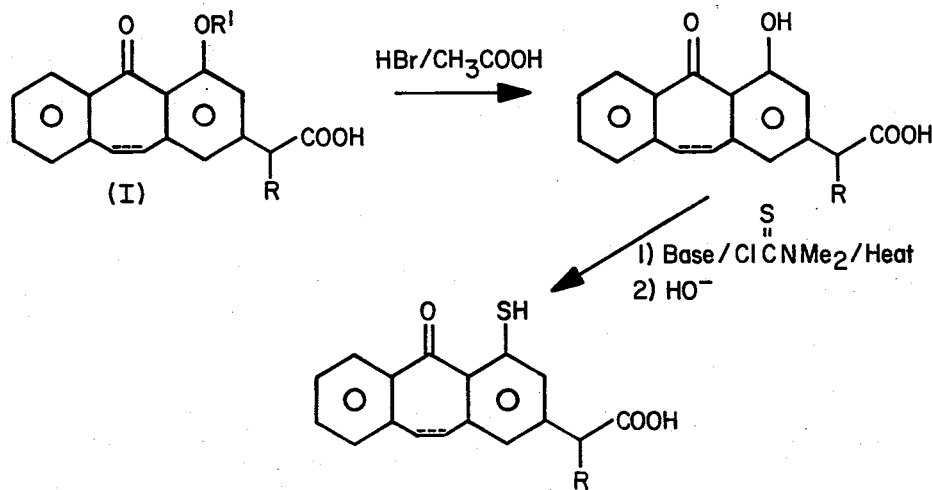
FIG_2

2,4-DISUBSTITUTED-5-OXO-5H-DIBENZO[a,d] CYCLOHEPTENES

FIELD OF THE INVENTION

This invention relates to novel chemical compounds. More particularly, this invention relates to novel, pharmaceutically active 5-oxo-5H-dibenzo[a,d]cycloheptene derivatives substituted at the 2- and 4-positions with a carboxylic acid moiety and an alcohol or thiol moiety respectively and esters and pharmaceutically acceptable salts thereof.

BACKGROUND OF THE INVENTION 10,11-Dihydro-5-oxo-5H-dibenzo[a,d]cycloheptene-3-acetic acid, the 3-α-substituted acetic acids and esters and salts thereof having anti-inflammatory activity are disclosed in U.S. Pat. No. 3,780,061. 10,11-Dihydro-5-oxo-5H-dibenzo[a,d]cycloheptene-2-acetic acid, the 2-α-substituted acetic acids and esters and salts thereof having anti-inflammatory activity are shown by West German OLS No. 2,409,919. Other related art can be found in U.S. Pat. No. 4,020,094.

SUMMARY OF THE INVENTION

The novel 5-oxo-5H-dibenzo[a,d]cycloheptene-2,4-di-substituted derivatives of the present invention can be represented by the following formula:

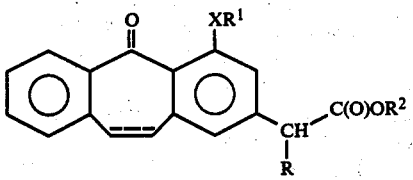

wherein R is hydrogen or methyl; $R^1$ is hydrogen, $C_1$ to $C_8$ linear or branched alkyl or $C_1$ to $C_8$ linear or branched alkanoyl; X is oxygen or sulfur; $R^2$ is selected from the group hydrogen, $C_1$ to $C_{18}$ linear or branched alkyl and the radicals $—(CH_2)_n—NR^3R^4$, $—CH_2—CH(OH)—CH_2OH$ or a ketal thereof formed from the aldehyde or ketone $R^5R^6CO$ wherein $R^3$ and $R^4$ are each independently $C_1$ to $C_6$ linear or branched alkyl or $R^3$ and $R^4$ taken together with the nitrogen atom of the first radical form a 5- or 6-membered heterocyclic ring, $R^5$ and $R^6$ are each independently hydrogen, $C_1$ to $C_6$ linear or branched alkyl, phenyl or benzyl or $R^5$ and $R^6$ taken together represent an alkylene bridge of from 4 to 6 carbon atoms; n is an integer of from 2 to 4; and the dotted line represents an optional double bond; and the pharmaceutically acceptable salts thereof.

In the compounds of the present invention of formula (I), it is preferred that X is oxygen and $R^1$ is selected from the group hydrogen, $C_1$ to $C_4$ linear or branched alkyl and $C_1$ to $C_4$ linear or branched alkanoyl. Most preferably $R^1$ is selected from the group hydrogen, methyl, ethyl, acetyl and propionyl.

In the compounds of formula (I) where R is hydrogen or methyl, $R^2$ is preferably selected from the group hydrogen, $C_1$ to $C_6$ linear or branched alkyl, most preferably methyl or ethyl; the radical $—(CH_2)_nNR^3NR^4$ where n is is the integer 2 or 3 most preferably 2, $R^3$ and $R^4$ are independently methyl or ethyl or taken together with the nitrogen atom of the radical is the group piperidino; and the radical $—CH_2CH(OH)CH_2OH$ or a ketal thereof formed from the aldehyde or ketone $R^5R^6CO$ where $R^5$ and $R^6$ are each independently hydrogen, methyl, ethyl, benzyl or phenyl, most preferably methyl.

Particularly preferred compounds of the present invention of formula (I) are:
4-mercapto-10,11-dihydro-5-oxo-5H-dibenzo[a,d]cyclohepten-2-yl acetic acid;
4-hydroxy-10,11-dihydro-5-oxo-5H-dibenzo[a,d]cyclohepten-2-yl acetic acid;
4-methoxy-10,11-dihydro-5-oxo-5H-dibenzo[a,d]cyclohepten-2-yl acetic acid;
4-ethoxy-10,11-dihydro-5-oxo-5H-dibenzo[a,d]cyclohepten-2-yl acetic acid;
4-acetoxy-10,11-dihydro-5-oxo-5H-dibenzo[a,d]cyclohepten-2-yl acetic acid;
4-propionyloxy-10,11-dihydro-5-oxo-5H-dibenzo[a,d]cyclohepten-2-yl acetic acid;
2-(4-hydroxy-10,11-dihydro-5-oxo-5H-dibenzo[a,d]cyclohepten-2-yl)propionic acid;
2-(4-methoxy-10,11-dihydro-5-oxo-5H-dibenzo[a,d]cyclohepten-2-yl)propionic acid;
2-(4-ethoxy-10,11-dihydro-5-oxo-5H-dibenzo[a,d]cyclohepten-2-yl)propionic acid;
2-(4-acetoxy-10,11-dihydro-5-oxo-5H-dibenzo[a,d]cyclohepten-2-yl)propionic acid;
2-(4-propionyloxy-10,11-dihydro-5-oxo-5H-dibenzo[a,d]cyclohepten-2-yl)propionic acid;
methyl 4-hydroxy-10,11-dihydro-5-oxo-5H-dibenzo[a,d]cyclohepten-2-yl acetate;
methyl 4-methoxy-10,11-dihydro-5-oxo-5H-dibenzo[a,d]cyclohepten-2-yl acetate;
methyl 4-ethoxy-10,11-dihydro-5-oxo-5H-dibenzo[a,d]cyclohepten-2-yl acetate;
methyl 4-acetoxy-10,11-dihydro-5-oxo-5H-dibenzo[a,d]cyclohepten-2-yl acetate;
methyl 4-propionyloxy-10,11-dihydro-5-oxo-5H-dibenzo[a,d]cyclohepten-2-yl acetate;
methyl 2-(4-hydroxy-10,11-dihydro-5-oxo-5H-dibenzo[a,d]cyclohepten-2-yl) propionate;
methyl 2-(4-methoxy-10,11-dihydro-5-oxo-5H-dibenzo[a,d]cyclohepten-2-yl) propionate;
methyl 2-(4-ethoxy-10,11-dihydro-5-oxo-5H-dibenzo[a,d]cyclohepten-2-yl) propionate;
methyl 2-(4-acetoxy-10,11-dihydro-5-oxo-5H-dibenzo[a,d]cyclohepten-2-yl) propionate;
methyl 2-(4-propionyloxy-10,11-dihydro-5-oxo-5H-dibenzo[a,d]cyclohepten-2-yl) propionate;
N,N-dimethylaminoethyl 4-hydroxy-10,11-dihydro-5-oxo-5H-dibenzo[a,d]cyclohepten-2-yl acetate;
N,N-dimethylaminoethyl 4-methoxy-10,11-dihydro-5-oxo-5H-dibenzo[a,d]cyclohepten-2-yl acetate;
N,N-dimethylaminoethyl 4-ethoxy-10,11-dihydro-5-oxo-5H-dibenzo[a,d]cyclohepten-2-yl acetate;
N,N-dimethylaminoethyl 4-acetoxy-10,11-dihydro-5-oxo-5H-dibenzo[a,d]cyclohepten-2-yl acetate;
N,N-dimethylaminoethyl 4-propionyloxy-10,11-dihydro-5-oxo-5H-dibenzo[a,d]cyclohepten-2-yl acetate;
2-(N-piperidino)ethyl 4-hydroxy-10,11-dihydro-5-oxo-5H-dibenzo[a,d]cyclohepten-2-yl acetate;
2-(N-piperidino)ethyl 4-methoxy-10,11-dihydro-5-oxo-5H-dibenzo[a,d]cyclohepten-2-yl acetate;
2-(N-piperidino)ethyl 4-ethoxy-10,11-dihydro-5-oxo-5H-dibenzo[a,d]cyclohepten-2-yl acetate;
2-(N-piperidino)ethyl 4-acetoxy-10,11-dihydro-5-oxo-5H-dibenzo[a,d]cyclohepten-2-yl acetate;
2-(N-piperidino)ethyl 4-propionyloxy-10,11-dihydro-5-oxo-5H-dibenzo[a,d]cyclohepten-2-yl acetate;

2,2-dimethyl-1,3-dioxolan-4-ylmethyl 4-hydroxy-10,11-dihydro-5-oxo-5H-dibenzo[a,d]cyclohepten-2-yl acetate;

2,2-dimethyl-1,3-dioxolan-4-ylmethyl 4-methoxy-10,11-dihydro-5-oxo-5H-dibenzo[a,d]cyclohepten-2-yl acetate;

2,2-dimethyl-1,3-dioxolan-4-ylmethyl 4-ethoxy-10,11-dihydro-5-oxo-5H-dibenzo[a,d]cyclohepten-2-yl acetate;

2,2-dimethyl-1,3-dioxolan-4-ylmethyl 4-acetoxy-10,11-dihydro-5-oxo-5H-dibenzo[a,d]cyclohepten-2-yl acetate;

2,2-dimethyl-1,3-dioxolan-4-ylmethyl 4-propionyloxy-10,11-dihydro-5-oxo-5H-dibenzo[a,d]cyclohepten-2-yl acetate;

4-hydroxy-5-oxo-5H-dibenzo[a,d]cyclohepten-2-yl acetic acid;

4-methoxy-5-oxo-5H-dibenzo[a,d]cyclohepten-2-yl acetic acid;

4-ethoxy-5-oxo-5H-dibenzo[a,d]cyclohepten-2-yl acetic acid;

4-acetoxy-5-oxo-5H-dibenzo[a,d]cyclohepten-2-yl acetic acid;

4-propionyloxy-5-oxo-5H-dibenzo[a,d]cyclohepten-2-yl acetic acid;

2-(4-mercapto-5-oxo-5H-dibenzo[a,d]cyclohepten-2-yl)propionic acid;

2-(4-hydroxy-5-oxo-5H-dibenzo[a,d]cyclohepten-2-yl)propionic acid;

2-(4-methoxy-5-oxo-5H-dibenzo[a,d]cyclohepten-2-yl)propionic acid;

2-(4-ethoxy-5-oxo-5H-dibenzo[a,d]cyclohepten-2-yl)propionic acid;

2-(4-acetoxy-5-oxo-5H-dibenzo[a,d]cyclohepten-2-yl)propionic acid;

2-(4-propionyloxy-5-oxo-5H-dibenzo[a,d]cyclohepten-2-yl)propionic acid;

methyl 4-hydroxy-5-oxo-5H-dibenzo[a,d]cyclohepten-2-yl acetate;

methyl 4-methoxy-5-oxo-5H-dibenzo[a,d]cyclohepten-2-yl acetate;

methyl 4-ethoxy-5-oxo-5H-dibenzo[a,d]cyclohepten-2-yl acetate;

methyl 4-acetoxy-5-oxo-5H-dibenzo[a,d]cyclohepten-2-yl acetate;

methyl 4-propionyloxy-5-oxo-5H-dibenzo[a,d]cyclohepten-2-yl acetate;

methyl 2-(4-hydroxy-5-oxo-5H-dibenzo[a,d]cyclohepten-2-yl) propionate;

methyl 2-(4-methoxy-5-oxo-5H-dibenzo[a,d]cyclohepten-2-yl) propionate;

methyl 2-(4-ethoxy-5-oxo-5H-dibenzo[a,d]cyclohepten-2-yl) propionate;

methyl 2-(4-acetoxy-5-oxo-5H-dibenzo[a,d]cyclohepten-2-yl) propionate;

methyl 2-(4-propionyloxy-5-oxo-5H-dibenzo[a,d]cyclohepten-2-yl) propionate;

N,N-dimethylaminoethyl 4-hydroxy-5-oxo-5H-dibenzo-[a,d]cyclohepten-2-yl acetate;

N,N-dimethylaminoethyl 4-methoxy-5-oxo-5H-dibenzo-[a,d]cyclohepten-2-yl acetate;

N,N-dimethylaminoethyl 4-ethoxy-5-oxo-5H-dibenzo[a,d]cyclohepten-2-yl acetate;

N,N-dimethylaminoethyl 4-acetoxy-5-oxo-5H-dibenzo-[a,d]cyclohepten-2-yl acetate;

N,N-dimethylaminoethyl 4-propionyloxy-5-oxo-5H-dibenzo[a,d]cyclohepten-2-yl acetate, 2-(N-piperidino)ethyl 4-hydroxy-5-oxo-5H-dibenzo[a,d]cyclohepten-2-yl acetate;

2-(N-piperidino)ethyl 4-methoxy-5-oxo-5H-dibenzo[a,d]cyclohepten-2-yl acetate;

2-(N-piperidino)ethyl 4-ethoxy-5-oxo-5H-dibenzo-[a,d]cyclohepten-2-yl acetate;

2-(N-piperidino)ethyl 4-acetoxy-5-oxo-5H-dibenzo-[a,d]cyclohepten-2-yl acetate;

2-(N-piperidino)ethyl 4-propionyloxy-5-oxo-5H-dibenzo[a,d]cyclohepten-2-yl acetate;

2,2-dimethyl-1,3-dioxolan-4-ylmethyl 4-hydroxy-5-oxo-5H-dibenzo[a,d]cyclohepten-2-yl acetate;

2,2-dimethyl-1,3-dioxolan-4-ylmethyl 4-methoxy-5-oxo-5H-dibenzo[a,d]cyclohepten-2-yl acetate;

2,2-dimethyl-1,3-dioxolan-4-ylmethyl 4-ethoxy-5-oxo-5H-dibenzo[a,d]cyclohepten-2-yl acetate;

2,2-dimethyl-1,3-dioxolan-4-ylmethyl 4-acetoxy-5-oxo-5H-dibenzo[a,d]cyclohepten-2-yl acetate; and 2,2-dimethyl-1,3-dioxolan-4-ylmethyl 4-propionyloxy-5-oxo-5H-dibenzo[a,d]cyclohepten-2-yl acetate.

When R is other than hydrogen, the compounds of formula (I) exist as pairs of enantiomorphs. Each enantiomorph or optical isomer and mixtures thereof are included within the present invention. The compounds of formula (I) which exist as pairs of enantiomorphs can be administered as racemic mixtures or they can be administered as resolved enantiomorphs. In some instances, one enantiomorph exhibits greater anti-inflammatory, analgesic and/or anti-pyretic activity than the other corresponding enantiomorphs.

In cases where $R^2$ is a ketal of the radical —CH$_2$CH(OH)CH$_2$OH as disclosed previously, an additional assymetric center is introduced into the compounds of formula (I). In compounds bearing this additional assymetry, four discrete stereoisomers are possible (2 enantiomorphic pairs). As in the case of the compounds with one assymetric center, these multi-assymetric centered compounds may also have one enantiomorph displaying enhanced physiologic activity.

The optical isomers, whether bearing one or two assymetric carbon atoms, can be resolved by conventional means, such as selective biological degradation or by the preparation of diastereoisomeric salts or esters of the carboxylic acid with an optically active amine base, such as 1-amphetamine or an optically active alcohol such as d-α-phenylethanol and separating the diastereoisomers by fractional crystallization. The separated diastereoisomeric salts or esters are then cleaved to yield the respective optical isomers.

The compounds of formula (I) exhibit anti-inflammatory, analgesic and anti-pyretic activity in mammals. Accordingly, the compositions of this invention are useful in the treatment and elimination of inflammation such as inflammatory conditions of the musclar skeletal system, skeletal joints and other tissues, for example, in the treatment of inflammatory conditions such as rheumatism, concussion, laceration, arthritis, bone fractures, post-traumatic conditions and gout. In those cases in which the above conditions include pain and pyrexia coupled with inflammation, the instant compounds are useful for the relief of these conditions as well as the inflammation.

Administration of the active compounds of formula (I) in an appropriate pharmaceutical composition can be via any of the accepted modes of administration of agents for the treatment of inflammation, pain or pyrexia. Thus, administration can be, for example, orally, parenterally or topically, in the form of solid, semi-solid or liquid dosage form, such as, for example, tablets, suppositories, pills, capsules, powders, liquid solutions, suspensions, creams, lotions, ointments or the like, preferably in unit dosage forms suitable for simple administration of precise dosages. The compositions of this invention may include a conventional pharmaceutical carrier or excipient and an active compound of formula (I), and, in addition, may include other medicinal agents, pharmaceutical agents, carriers, adjuvants, etc.

The preferred manner of administration of the compounds of the present invention is oral using a convenient daily dosage regimen which can be adjusted according to the degree of affliction. Generally, a daily dose of from 0.05 mg. to 10 mg. of active compound of formula (I) per kilogram of body weight is used. Most conditions respond to treatment comprising a dosage level of the order of 0.5 mg. to 5 mg per kilogram of body weight per day. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, sucrose, magnesium carbonate and the like. Such compositions take the form of solutions, suspensions, tablets, pills, capsules, powders, sustained release formulations and the like.

The active compound of formula (I) may be formulated into a suppository using, for example, polyalkylene glycols, for example, polypropylene glycol, as the carrier. Liquid pharmaceutically administrable compositions can, for example, be prepared by dissolving, dispersing, etc. an active compound of formula (I) and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pa., 14th Edition, 1970. The composition to be administered will, in any event, contain a quantity of the active compound(s) in a pharmaceutically effective amount for relief of the particular condition being treated in accordance with the teachings of this invention.

The compounds of formula (I) are also uterine smooth muscle relaxants and thus are useful as agents for maintaining the pregnancy of pregnant mammals, for the benefit of the mother and/or the fetus, until termination of the pregnancy is considered from a medical point of view to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

The compounds of formula (I) are also used as agents for delaying the onset of, or for postponing, parturition. As used in this application, the phrase "to delay on the onset of parturition" is intended to cover that delay in parturition caused by the administration of a compound of formula (I) at any time before uterine muscle contractions have begun. Thus, it is intended that the aforementioned phrase covers abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e. delivery prior to full term). Such administration is also useful where there are clinical indications that the pregnancy might be terminated prior to that time considered favorable to the mother and/or fetus.

As used in this application, the phrase "postponing parturition" is intended to mean that delay in parturition caused by the administration of a compound of formula (I) after uterine muscle contractions have begun. The condition of the patient, including the time within the gestation period when the contractions have begun, the severity of the contractions and how long the contractions have taken place will affect the results achieved with the administration of a compound of formula (I). For example, this effect can be to reduce the intensity and/or the duration of the contractions (the actual act of parturition being "prolonged") or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother or to occur at a more appropriate time and/or place.

With respect to animals, this treatment can also be utilized to synchronize deliveries from a group of pregnant animals to happen at or about the same time, or to happen at or about a desired time and/or place, thereby allowing the births to be handled with greater facility.

In all cases, administration of a compound of formula (I) for these purposes should be consistent with best and/or accepted medical (or veterinary) practices so as to maximize the benefits to the mother and the fetus. For example, administration should not be continued so long past full term that the fetus dies in utero.

In the practice of this aspect of the present invention, a therapeutically effective amount of a compound of formula (I) or a pharmaceutical composition containing a compound of formula (I) is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally or parenterally in the doses and in the forms (including oral, vaginal or uterine tablets or suppositories, etc.) as set forth above regarding anti-inflammatory, etc. activities. Administration can be a single daily dose or up to three or four smaller doses regularly given throughout the day. The actual amount of active compound administered will, of course, depend on its relative activity for this particular utility.

The compound of formula (I) can be prepared by conducting an Arndt-Eistert reaction upon 4-$XR^1$-5-oxo-5H-dibenzo[a,d]cycloheptene-2-carboxylic acid or upon its 10,11-dihydro analog to afford the 4—$XR^1$ substituted-5-oxo-5H-dibenzo[a,d]cycloheptene-2-acetic acid, its esters, amides or ketals. The 10,11-dihydro analogs thereof can be obtained from these latter compounds. 2-(4-$XR^1$ substituted-5-oxo-5H-dibenzo[a,d]cyclohepten-2-yl)propionic acids, the corresponding esters and ketals thereof of the aforementioned acids can be obtained by alkylation and/or esterification of the cycloheptene-2-acetic acids.

A better understanding of the present invention can be had by referring to the Detailed Description of the Preferred Embodiments in connection with the accompanying drawing in which:

FIG. 1. illustrates a reaction sequence useful for preparation of the compounds of formula (I).

FIG. 2. illustrates a further reaction sequence useful for preparation of the compounds of formula (I).

Referring now to FIG. 1, a reaction scheme is illustrated in which the compounds of the present invention can be prepared. While the disclosures specifically set forth in the discussion to follow are in regard to the 4—$OR^1$ sustituted-5-oxo-5H-dibenzo[a,d]cycloheptene nucleus, it should be understood that the 10,11-dihydro analogs also undergo substantially identical reactions. Step 1 illustrates the initial reaction used to elongate the carboxylic acid chain of the starting 4-$OR^1$-dibenzo[a,d]cycloheptene-2-carboxylic acid, i.e. the Arndt-Eistert reaction where the carboxylic acid is first treated typically at 0° to 75° with thionyl chloride to obtain the acid chloride. As a second step in this classical reaction, the acid chloride is reacted at from about −20° to about +20°, preferably about 0° with diazomethane to form a diazoketone which in turn is rearranged by the action of a silver salt in the presence of an alcohol, for example, methanol or ethanol (step 3, FIG. 1). The resulting alkyl 4-$OR^1$ substituted-5-oxo-5H-dibenzo[a,d]cyclohepten-2-yl acetate is hydrolyzed to afford the 2-acetic acid (except when $R^1$=H) as illustrated in step 4 Compound (I)i. The 4-$OR^1$-5-oxo-5H-dibenzo[a,d]-cycloheptene-2-yl acetic acid (Compound (I)i) may be esterified with the alkyl iodide, $R^2I$, Compound (I)ii. Compounds (I)ii are readily converted to the compounds of the present invention where $R^1$ is $C_1$ to $C_8$ linear or branched alkanoyl by conventional esterification procsses. For example, by reaction of Compounds (I)ii with ($R^1$=H) with an acid chloride; an acid anhydride; by catalyzed or uncatalyzed direct esterification; or by transesterification. Compounds (I)ii when treated with an anion-forming base and an alkyl halide, such as methyl iodide or methyl bromide, α-alkylate bromide, α-alkylate the 2-acetic acid ester side chain, and form the 2-propionic acid ester (Compound (I)iii, where R=$CH_3$) (step 6). The esters formed, (I)iii, can then be hydrolyzed to the free carboxylic acid as shown in step 7, compound (I)iv, R=$CH_3$. The 4-methoxy-5-oxo-dibenzo[a,d]cyclohepten-2-yl acetic or propionic acids of step 4 or step 7 (Compounds (I)i and (I)iv) can further be subjected to hydrolytic cleavage to form the compounds of the present invention bearing a 4-hydroxyl. See FIG. 2.

The compounds of the present invention where X=oxygen are also useful intermediates in the synthesis of the compounds of the present invention of formula (I) where X is sulfur. As illustrated in FIG. 2, Compound (I) when treated with base and N,N-dimethylthiocarbamoyl chloride undergoes substitution and, upon heating, rearranges to the compounds of formula (I) wherein the group $XR^1$=SH. This reaction is set forth in more detail in Example 5 and in the literature. Compounds of formula (I) where X is S and $R^1$ is other than hydrogen can be readily prepared from this thiol by reactions similar to those of the oxygenated analogs, e.g., base catalyzed reaction of alkyl halides or acyl halides with the 4-mercapto compounds.

The Arndt-Eistert reaction discussed briefly above is a well-known series of reaction steps, the particulars of which can be determined by reference to the Examples below or to the articles thereon in the published literature. The free acids, i.e., compounds (I)(i), (I)ii and (I)iv can be esterified according to known procedures, for example, by treatment of the free acid or one of its functional derivatives, such as the acid chloride or the acid anhydride with an appropriate alcohol in the presence of an acid, dehydrating or basic catalyst. Other methods of esterification or transesterification known to those skilled in the art can also be utilized. Alkyl esters wherein the alkyl ester moiety has 13 to 18 carbon atoms as prepared with, for example, tridecanol, 7-tridecanol, tetradecanol, pentadecanol, 2-pentadecanol, hexadecanol, heptadecanol, 2-heptadecanol, octadecanol and 2-octadecanol, are also considered to be within the scope of this invention.

Also included within the novel compounds of formula (I) are the corresponding dialkylaminoalkyl esters thereof which can be prepared by converting the free acid compound to the corresponding acid halide, as by treatment with thionyl chloride, and reacting the acid halide so produced with the hydroxyalkylamine such as 2-(N,N-dimethylamino)-ethanol or 2-(N,N-diethylamino)ethanol and the like, to afford the compounds of formula (I) wherein $R^3$ and $R^4$ are independently $C_1$ to $C_6$ linear or branched alkyl. The acid halide derivatives can also be reacted with N-(omegahydroxyalkyl)heterocyclic amines to afford the compounds of formula (I) where $R^3$ and $R^4$ and the nitrogen atom to which they are attached form a heterocyclic ring.

The starting materials shown in FIG. 1, i.e. 4-$OR^1$-5-oxo-5H-dibenzo[a,d]cycloheptene-2-carboxylic acid, as well as its 10,11-analog, are prepared by simultaneously etherifying and esterifying 2-hydroxy-6-methyl terephthalic acid with methyl iodide. The corresponding dimethyl 2-methoxy-6-methylterephthalate is, in turn, reacted with N-bromosuccinimide to afford the dimethyl 2-methoxy-6-bromomethylterephthalate which in turn is reacted with triphenylphosphine to afford 3-methoxy-2,5-bis(carbomethoxy)benzyltriphenylphosphonium bromide. This latter compound is treated with benzaldehyde and 1,5-diazabicyclo[4.3.0]non-5-ene to afford, after alkaline hydrolysis, a mixture of cis- and trans-3-methoxy stilbene-2,5-dicarboxylic acids. Hydrogenation of this cis-, trans-mixture typically with hydrogen over palladium on carbon catalyst, affords 2-methoxy-6-phenethylterephthalic acid. Treatment of this latter compound with polyphosphoric acid yields 4-methoxy-10,11-dihydro-5-oxo-5H-dibenzo[a,d]cycloheptene-2-carboxylic acid, i.e. one of the possible starting materials shown in FIG. 1, step 1 for preparing the compounds of the present invention not bearing a double bond at the 10,11-position of the dibenzo[a,d]cycloheptene ring. Unsaturation can be produced at this position by first esterifying the dihydrodibenzocycloheptene carboxylic acid with diazomethane, forming the methyl ester and treating this ester with N-bromosuccinimide/irradiation, followed by 1,5-diazabicyclo[4.3.0]non-5-ene, thereby resulting in hydrogen bromide abstraction at the 10,11-position and forming methyl 4-methoxy-5-oxo-5H-dibenzo[a,d]cycloheptene-2-carboxylate. The free acid is readily formed by basic hydrolysis with an alkali metal hydroxide or carbonate in the classical manner of ester cleavage rections. These reactions are set forth in greater detail in the Preparations herein and in U.S. Pat. No. 4,020,094, incorporated herein by reference.

As used herein, the term "heterocyclic ring" refers to both unsubstituted and substituted heterocyclic rings containing at least one nitrogen atom and includes both saturated and unsaturated heterocyclic rings having 5 or 6 ring atoms. More specifically, the heterocyclic rings per se contemplated hereby have one nitrogen atom and 4 or 5 carbon atoms, 2 nitrogen atoms and 3 or 4 carbon atoms or 1 nitrogen atom, 1 oxygen atom and 4 carbon atoms. Typical heterocyclic rings include, for example, the groups pyrrolidinyl, 2-methylpyrrolidin-1-yl, morpholino, 3-methylmorpholino, 4-N-methylpiperazin-1-yl, 4-(N-$\beta$-hydroxyethyl)piperazin-1-yl, piperidinyl and the like.

The term "$C_1$ to $C_6$ linear or branched alkyl" refers to both straight and branched alkyl groups having from 1 to 6 carbon atoms and thus includes primary, secondary and tertiary alkyl groups. Typical alkyl groups include for example, methyl, ethyl, n-propyl, isopropyl, n-butyl, isobutyl, t-butyl, n-amyl, n-hexyl and the like.

The term "pharmaceutically acceptable salts" refers to salts prepared from pharmaceutically acceptable, non-toxic bases including inorganic bases and organic bases. Salts derived from inorganic bases include sodium, potassium, lithium, ammonium, calcium, magnesium, ferrous, zinc, manganous, aluminum, ferric, manganic salts and the like. Copper salts are also contemplated herein. Salts derived from pharmaceutically acceptable, organic, non-toxic bases include salts of primary, secondary, tertiary and quaternary amines, substituted amines including naturally occurring substituted amines, cyclic amines and basic ion-exchange resins. Examples include triethylamine, tripropylamine, 2-(N,N-dimethylamino)-ethanol, 2-(N,N-diethylamino)ethanol, ethanolamine, lysine, arginine, histidine, caffeine, procaine, n-ethylpiperi-dine, hydrabamine, choline, betaine, ethylenediamine, glucosamine, methylglucamine, theobromine, purines, piper- azine, piperidine resins and the like. The isopropylamine salts are also contemplated herein.

In each of the process steps described hereinabove and below, unless otherwise indicated, the respective intermediate products are preferably separated from the reaction mixture and purified prior to their use as a starting material for the next step in the process. Such separation and purification can be effected by any suitable procedure. For example, typical separation procedures include filtration, extraction, evaporation and other typical purification procedures including crystallization and thin-layer as well as column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above and then selecting a particular reaction step(s), as for example described, above to give the compound desired. In view of this disclosure, the preparation of particular compounds, including compounds falling within the present invention but not specifically described in the specification will be apparent to those skilled in this art.

DETAILED DESCRIPTION OF THE PREFERRED EMBODIMENTS

The following detailed description is given to enable those skilled in the art to more clearly understand and practice the present invention. It should not be considered as a limitation upon the scope of the invention but merely as being illustrative and representative thereof. All temperatures are in degrees Centigrade unless otherwise specified.

PREPARATION 1

(a) 2-Hydroxy-6-methylterephthalic acid (1.0 g) is dissolved in dimethylformamide (20 ml) and potassium carbonate (2.0 g) and methyl iodide (5.0 ml) are added. The mixture is stirred at 25° for 16 hours, then poured into water and extracted with ethyl acetate. The extract is washed with water, dried and evaporated. The product is recrystallized from ether-hexane to afford dimethyl 2-methoxy-6-methylterephthalate, mp 98°–99°.

(b) Dimethyl 2-methoxy-6-methylterephthalate (2.0 g) is dissolved in carbon tetrachloride (50 ml) and N-bromosuccinimide (1.5 g) is added. The solution is refluxed and illuminated with a 100 watt incandescent lamp for 3 hours, then cooled, filtered and evaporated. The residue is dissolved in acetonitrile (30 ml) and triphenylphosphine (3.2 g) is added. The solution is refluxed for 3 hours, cooled and reduced in volume to about 20 ml, then diluted with ether (about 20 ml). The solid is filtered off and dried under vacuum to afford 3-methoxy-2,5-bis(carbomethoxy)benzyltriphenylphosphonium bromide, mp 147°–149°.

(c) 3-Methoxy-2,5-bis(carbomethoxy)benzyltriphenylphosphonium bromide (50 g) is dissolved in dimethylformamide (400 ml) and sodium hydride (4.5 g of a 50% oil dispersion) is added. After hydrogen evolution has stopped, benzaldehyde (20 ml) is added. The mixture is allowed to stand at 25° for 16 hours, then poured into water and extracted with ethyl acetate (3x). The extract is washed, dried and evaporated. The residue is refluxed in water (200 ml) and methanol (40 ml) containing sodium hydroxide (20 g.) for 6 hours, then cooled, washed with ether and acidified with 2 N hydrochloric acid. The aqueous solution is extracted with ethyl acetate and the extract washed, dried and evaporated to afford cis- and trans-3-methoxystilbene-2,5-dicarboxylic acid.

(d) The products of part (c) (19.3 g) are dissolved in dimethylformamide (100 ml) and acetic acid (100 ml) and hydrogenated at 40 psi for 8 hours using 10% palladium on carbon (1.0 g) as catalyst. The mixture is filtered through celite, poured into water and extracted with ethyl acetate. The extract is washed, dried and evaporated. The residue is recrystallized from aqueous methanol to afford 2-methoxy-6-phenethylterephthalic acid, mp 242°–244°.

(d) 2-Methoxy-6-phenethylterephathlic acid (40 g) is dissolved in sulfolane (350 ml) at 130° and polyphosphoric acid (200 ml) is added. The solution is stirred at 130° for 3 hours, then cooled and poured into water. The solution is extracted with ethyl acetate; the extract washed with water, dried and evaporated. The residue is recrystallized from aqueous methanol to afford 4-methoxy-10,11-dihydro-5-oxo-5H-dibenzo[a,d]cycloheptene-2-carboxylic acid, mp 222°–227°.

PREPARATION 2

4-Methoxy-10,11-dihydro-5-oxo-5H-dibenzo[a.d]cycloheptene-2-carboxylic acid (4.0 g) is dissolved in dimethylformamide (30 ml) and to the solution is added excess ethereal diazomethane. The mixture is evaporated to low volume, poured into water and extracted with ethyl acetate. The extract is washed, dried and evaporated to yield methyl 4-methoxy-10,11-dihydro-5-oxo-5H-dibenzo[a,d]cycloheptene-2-carboxylate. 1.0 G of this compound is refluxed for 1 hour in carbon tetrachloride (50 ml) containing N-bromosuccinimide (0.635 g) while irradiating the mixture with a 100 watt incandescent lamp. The solution is cooled, filtered and evaporated. The residue is dissolved in dimethylformamide (10 ml) and 1,5-diazabicyclo[4.3.0]non-5-ene (1.0 ml) is added. The mixture is heated to 70° for 30 minutes then cooled and poured into water. The solution is extracted with ethyl acetate, and the extract washed, dried and evaporated to afford methyl 4-methoxy-5-oxo-5H-dibenzo[a,d]cycloheptene-2-carboxylate. This material is refluxed for 3 hours in water (10 ml) and methanol (2.5 ml) containing sodium hydroxide (0.5 g). The cooled solution is acidified with 2 N hydrochloric acid and extracted with ethyl acetate. The extract is dried and evaporated. The residue is recrystallized from aqueous methanol to afford 4-methoxy-5-oxo-5H-dibenzo[a,d]cycloheptene-2-carboxylic acid, mp 252°–253°.

EXAMPLE 1

(a) 4-Methoxy-10,11-dihydro-5-oxo-5H-dibenzo[a,d]cycloheptene-2-carboxylic acid (4.1 g) is stirred in a mixture of chloroform (125 ml), thionyl chloride (4 ml) and dimethylformamide (0.2 ml) for 4 hours. The solution is evaporated to dryness and the residue dissolved in chloroform (100 ml). To this solution, at 0°, is added about 100 ml of an ethereal solution of diazomethane (about 0.5 g). The precipitate is filtered and dried to afford 2-diazoacetyl-4-methoxy-10,11-dihydro-5-oxo-5H-dibenzo[a,d]cycloheptene.

(b) 2-Diazoacetyl-4-methoxy-10,11-dihydro-5-oxo-5H-dibenzo[a,d]cycloheptene is dissolved in refluxing ethanol (75 ml) and to the solution is added silver benzoate (0.45 g). Reflux is continued for 5 minutes. The solution is cooled and filtered through celite, then evaporated. The residue is chromatographed on silica gel (25 g), eluting with 1:1 ethyl acetate:hexane, to afford ethyl 4-methoxy-10,11-dihydro-5-oxo-5H-dibenzo[a,d]cyclohepten-2-acetate as an oil.

(c) Ethyl 4-methoxy-10,11-dihydro-5-oxo-5H-dibenzo[a,d]cyclohepten-2-acetate is refluxed in water (20 ml) and methanol (5 ml) containing sodium hydroxide (0.5 g) for 2 hours. The solution is cooled, acidified with 2 N hydrochloric acid and extracted with ethyl acetate. The extract is washed, dried and evaporated. The residue is recrystallized from ethyl acetate-hexane to afford 4-methoxy-10,11-dihydro-5-oxo-5H-dibenzo[a,d]cyclohepten-2-yl acetic acid, mp 189°–199°.

Similarly prepared, starting with 4-methoxy-5-oxo-5H-dibenzo[a,d]cyclohepten-2-yl carboxylic acid is 4-methoxy-5-oxo-5H-dibenzo[a,d]cyclohepten-2-yl acetic acid, mp 213°–215°.

EXAMPLE 2

4-Methoxy-5-oxo-5H-dibenzo[a,d]cyclohepten-2-yl acetic acid (0.5 g) is dissolved in dimethylformamide (10 ml) and potassium carbonate (2.0 g) and methyl iodide (3 ml) are added. The mixture is stirred at 25° for 16 hours, then poured into water and the solution extracted with ethyl acetate. The extract is washed with water, dried and evaporated. The residue is chromatographed on silica gel (10 g), eluting with ethyl acetate:hexane (1:1), to afford methyl 4-methoxy-5-oxo-5H-dibenzo[a,d]-cyclohepten-2-yl acetate as an oil.

EXAMPLE 3

(a) Isopropylcyclohexylamine (0.278 ml) is added to tetrahydrofuran (5 ml), the solution cooled to −78° and 1.6 molar n-butyllithium in hexane (0.96 ml) is added. After 10 minutes, methyl 4-methoxy-5-oxo-5H-dibenzo[a,d]-cyclohepten-2-yl acetate (0.473 g) is added. The mixture is allowed to stand 30 minutes at −78° and methyl iodide (0.19 ml) is added. The reaction is maintained at −78° for 1 hour, warmed to 25°, poured into water and extracted with ethyl acetate. The extract is washed with water, dried and evaporated and the residue chromatographed on silica gel (20 g) eluting with hexane:ethyl acetate 2:1, afford methyl 2-(4-methoxy-5-oxo-5H-dibenzo[a,d]cyclohepten-2-yl)propionate as an oil.

(b) The product of step (a) is dissolved in tetrahydrofuran (10 ml) and 0.1 N aqueous sodium hydroxide (12 ml) is added. After 30 minutes the solution is added to water and washed with ether. The aqueous layer is acidified with 2 N hydrochloric acid and extracted with ethyl acetate. The extract is dried, evaporated and the residue chromatographed on silica gel (10 g) eluting with hexane:ethyl acetate:acetic acid 60:40:2, to afford dl-2-(4-methoxy-5-oxo-5H-dibenzo[a,d]cyclohepten-2-yl)-propionic acid, mp 144°–147° (ethyl acetate-hexane).

Similarly prepared, starting with 4-methoxy-10,11-dihydro-5-oxo-5H-dibenzo[a,d]cyclohepten-2-yl acetic acid is dl-2-(4-methoxy-10,11-dihydro-5-oxo-5H-dibenzo[a,d]-cyclohepten-2-yl)propionic acid, mp 173°–175° C.

EXAMPLE 4

4-Methoxy-10,11-dihydro-5-oxo-5H-dibenzo[a,d]cyclohepten-2-yl acetic acid (0.3 g) is refluxed in acetic acid (4.5 ml) and 48% aqueous hydrobromic acid (4.5 ml) for 30 minutes. The cooled solution is poured into water and extracted with ethyl acetate. The extract is washed, dried, evaporated and the residue recrystallized from ethyl acetate/hexane to afford 4-hydroxy-10,11-dihydro-5-oxo-5H-dibenzo[a,d]cyclohepten-2-yl acetic acid, mp 149°–151°.

Similarly prepared, using as starting materials:
4-methoxy-5-oxo-5H-dibenzo[a,d]cyclohepten-2-yl acetic acid;
2-(4-methoxy-10,11-dihydro-5-oxo-5H-dibenzo[a,d]cyclohepten-2-yl)propionic acid; and
2-(4-methoxy-5-oxo-5H-dibenzo[a,d]cyclohepten-2-yl)propionic acid are:
4-hydroxy-5-oxo-5H-dibenzo[a,d]cyclohepten-2-yl acetic acid, mp 187°–188°;
2-(4-hydroxy-10,11-dihydro-5-oxo-5H-dibenzo[a,d]cyclohepten-2-yl)propionic acid, mp 125°–126°; and
2-(4-hydroxy-5-oxo-5H-dibenzo[a.d]cyclohepten-2-yl)-propionic acid, mp 163°–165°.

EXAMPLE 5

Methyl 4-hydroxy-5-oxo-5H-dibenzo[a,d]cyclohepten-2-yl acetate (0.316 g) is dissolved in dimethylformamide (3 ml) and sodium hydride (0.052 g of a 58% oil dispersion) is added. After 20 minutes dimethylthiocarbamoyl chloride (0.13 g) is added. The mixture is heated to 80° for 4 hours, then added to dilute aqueous hydrochloric acid. The solution is extracted with ethyl acetate and the extract dried and evaporated. The residue is chromatographed on silica gel, eluting with 2:1 hexane:ether, so as to afford S-[2-(carbomethoxymethyl)-10,11-dihydro-5-oxo-5H-dibenzo[a,d]cyclohepten-4-yl]dimethylthiocarbamate as an oil. This material is refluxed for 1 hour in 2:1 aqueous methanol (5 ml) containing sodium hydroxide (0.2 g). The solution is cooled and washed with ether, then acidified with hydrochloric acid and extracted with ethyl acetate. The extract is washed with water, dried and evaporated to give 4-mercapto-5-oxo-5H-dibenzo[a,d]cyclohepten-2-yl acetic acid.

Similarly prepared from the 4-hydroxy compounds illustrated in Example 4 are:
4-mercapto-10,11-dihydro-5-oxo-5H-dibenzo[a,d]cyclohepten-2-yl acetic acid;
2-(4-mercapto-10,11-dihydro-5-oxo-5H-dibenzo[a,d]cyclohepten-2-yl)propionic acid; and
2-(4-mercapto-5-oxo-5H-dibenzo[a,d]cyclohepten-2-yl)-propionic acid.

While the present invention has been described with reference to specific embodiments thereof, it should be understood by those skilled in the art that various changes may be made and equivalents may be substituted without departing from the true spirit and scope of the invention. In addition, many modifications can be made to adapt a particular situation, material or composition of matter, process, process step or steps, or then-present objective to the spirit of this invention without departing from its essential teachings.

What is claimed is:

1. A compound selected from the group represented by the formula:

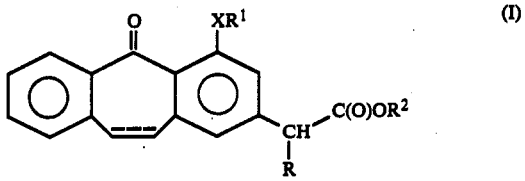

wherein R is hydrogen or methyl; $R^1$ is hydrogen, $C_1$ to $C_8$ linear or branched alkyl or $C_1$ to $C_8$ linear or branched alkanoyl; X is oxygen; $R^2$ is selected from the group hydrogen and $C_1$ to $C_{18}$ linear or branched alkyl; and the dotted line represents an optional double bond; and the pharmaceutically acceptable salts thereof.

2. The compound of claim 1 wherein R is hydrogen.
3. The compound of claim 2 wherein $R^2$ is hydrogen.
4. The compound of claim 2 wherein $R^2$ is $C_1$ to $C_{18}$ linear or branched alkyl.
5. The compound of claim 2 wherein $R^2$ is $C_1$ to $C_6$ linear or branched alkyl.
6. The compound of claim 5 wherein $R^2$ is methyl or ethyl.
7. The compound of claim 6 wherein $R^1$ is hydrogen.
8. The compounds of claim 3 wherein $R^1$ is methyl.
9. The compound of claim 1 wherein R is methyl.
10. The compound of claim 9 wherein $R^2$ is $C_1$ to $C_6$ linear or branched alkyl.
11. The compound of claim 10 wherein $R^2$ is methyl or ethyl.
12. The compound of claim 11 wherein $R^1$ is hydrogen.